(12) United States Patent
Lorenz et al.

(10) Patent No.: US 8,352,013 B2
(45) Date of Patent: Jan. 8, 2013

(54) METHOD AND SYSTEM FOR MOTION COMPENSATION IN MAGNETIC RESONANCE (MR) IMAGING

(75) Inventors: Christine Lorenz, Frederick, MD (US); Maneesh Dewan, Baltimore, MD (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 1167 days.

(21) Appl. No.: 11/313,598

(22) Filed: Dec. 21, 2005

(65) Prior Publication Data

US 2006/0183999 A1 Aug. 17, 2006

Related U.S. Application Data

(60) Provisional application No. 60/644,823, filed on Jan. 18, 2005.

(51) Int. Cl.
*A61B 5/05* (2006.01)

(52) U.S. Cl. .......................... 600/410; 600/413

(58) Field of Classification Search .................. 600/410, 600/411, 416, 509; 324/206, 212, 309
See application file for complete search history.

(56) References Cited

U.S. PATENT DOCUMENTS

| | | | | |
|---|---|---|---|---|
| 6,009,341 A * | 12/1999 | Edelman | ...................... | 600/413 |
| 6,057,680 A * | 5/2000 | Foo et al. | ...................... | 324/206 |
| 6,791,323 B2 * | 9/2004 | Wang et al. | ...................... | 324/309 |
| 6,924,643 B2 | 8/2005 | Sussman et al. | | |
| 7,469,160 B2 * | 12/2008 | Banks et al. | ...................... | 600/476 |
| 2002/0095085 A1 * | 7/2002 | Saranathan et al. | ........... | 600/413 |
| 2002/0156366 A1 * | 10/2002 | Stainsby et al. | ............... | 600/413 |
| 2005/0096543 A1 * | 5/2005 | Jackson et al. | ................ | 600/441 |

OTHER PUBLICATIONS

Shechter, Guy, "Respiratory Motion of the Heart from Free Breathing Coronary Angiograms" IEEE Transactions on Medical Imaging, vol. 23, No. 8, Aug. 8, 2004.*

Manke, Dirk et al., "Novel Prospective Respiratory Motion Correction Approach for Free-Breathing Coronary MR Angiography Using a Patient-Adapted Affine Motion Model," *Magnetic Resonance in Medicine* 50:122-131 (2003).

McLeish, Kate et al., "A Study of the Motion and Deformation of the Heart Due to Respiration," *IEEE Transactions on Medical Imaging*, 21:9, Sep. 2002.

Manke, Dirk et al., "Model Evaluation and Calibration for Prospective Respiratory Motion Correction in Coronary MR Angiography Based on 3-D Image Registration," *IEEE Transactions on Medical Imaging*, 21:9 Sep. 2002.

Manke, Dirk et al., "Respiratory Motion in Coronary Magnetic Resonance Angiography: A Comparison of Different Motion Models" *Journal of Magnetic Resonance Imaging* 15:661-671 (2002).

* cited by examiner

*Primary Examiner* — Unsu Jung
*Assistant Examiner* — Christopher Cook

(57) ABSTRACT

A method and system are provided for imaging by predicting, from multiple real time MR imaging data, motion of an object and subsequently obtaining high-resolution imaging data of the object using the predicted motion of the object. Thus, the process uses real time images to derive a history of the motion of the object and thereby generate a predicted trajectory of the object and then uses this trajectory to determine the projected position of the object during a subsequent, separate, high-resolution data acquisition phase.

9 Claims, 4 Drawing Sheets

METHOD AND SYSTEM FOR MOTION COMPENSATION IN MAGNETIC RESONANCE (MR) IMAGING

CROSS-REFERENCED TO RELATED APPLICATIONS

This application claims priority from U.S. Provisional application No. 60/644,823, filed Jan. 18, 2005, which is incorporated herein by reference.

TECHNICAL FIELD

This invention relates generally to magnetic resonance (MR) imaging and more particularly to motion compensation used in such MR imaging.

BACKGROUND

As is known in the art, motion compensation in body or neuro MR involves acquisition of low-resolution 2D or 3D image data and performing bulk registration of all features in the image to derive a transformation matrix to adjust the scanner's slice position. In the case of coronary motion compensation, the state of the art involves performing a 1D MR image with high temporal resolution to monitor the bulk motion of the diaphragm. In this case, 1D acquisition is used in place of 2D to attain sufficient temporal resolution. This diaphragm motion in turn is assumed to be linearly correlated with the motion of the heart, and in turn to be linearly correlated with the motion of the individual coronary arteries. However, clinical results and other studies analyzing cardiac and coronary motion clearly show that this is a false assumption, leading to blurring and motion artifacts when imaging the coronary arteries.

Several attempts to address the problem of determining motion of the heart for the purpose of imaging the coronary arteries have been suggested. One technique is sometimes referred to as an adaptive navigator technique. With such technique, raw data acquisition based on the motion magnitude is obtained and the location modified in k-space to minimize motion effects. There are also slice-following techniques that move the slice position of the scan based on motion detected by a 1D navigator.

Another suggested technique is sometimes referred to as a multiple navigator technique. Here, motion derived is used not only in one direction, but also from 3 directions to assess motion of the heart in 3D. This method still assumes that heart motion and coronary motion are correlated, and that there is no change in position between the time of the navigator measurement and the image acquisition.

Still another suggested technique uses low-resolution measurement and tracks bulk heart motion which, combined with 3 navigators, corrects for motion in 3 dimensions. The disadvantage of this method is that the 3D heart motion model is derived at a single time-point and not updated during subsequent high resolution scanning of the coronaries. In addition, it still assumes correlation between heart motion and coronary motion, and that the heart cycle length, and motion of the heart within each cycle is relatively constant. Such techniques are described in one or more of the following papers: "Novel Prospective Respiratory Motion Compensation Approach for Free-Breathing Coronary MR Angiography Using a Patient-Adapted Affine Model" by Dirk Manke, Kay Nehrke and Peter Boernert, published in Magnetic Resonance Medicine 50:122-131 (2003); "A Study of the Motion and Deformation of the Heart Due to Respiration" by Kate McLeish and Derek L. G. Hill, published in the IEEE Transactions on Medical Imaging, Vol. 21, No. 9, Sep. 2002; A Model Evaluation and Calibration for Protective Respiratory Correction in Coronary MR Angiography Based on 3-D Image Registration" by Dirk Manke, Peter Rosch, Kay Nehrke, Peter Bornert and Olaf Dossel, published in the IEEE Transactions on Medical Imaging Vol. 9, Sep. 2002; and "Respiratory Motion in Coronary Magnetic Resopnance Angiography" A Comparison of Different Models", by Dirk Manke, Kay Nehrke, Peter Bornert, Peter Rosch, and Olaf Dossel, published in the Journal of Magnetic Resonance 15-661-667 (2002)/

SUMMARY

In accordance with the present invention, a method is provided for imaging. The method includes predicting, from multiple real time imaging data, motion of an object and subsequently obtaining high-resolution imaging data of the object using the predicted motion of the object.

Thus, the process uses real time images to derive a history of the motion of the object and thereby generate a predicted trajectory of the object and then uses this trajectory to determine the projected position of the object during a subsequent, separate, high-resolution data acquisition phase.

With such method, motion of an object in MR imaging (for example, a coronary artery) is followed and the predicted motion (i.e., the predicted trajectory of the object) guides MR imaging during the subsequent, high-resolution imaging phase.

In one embodiment, the method includes extracting coronary position from images acquired using real time data. Using such real time data acquired images and electrocardiogram (ECG) data, the method builds a model of coronary motion using the real time image data based on the current and past heartbeats obtained using the ECG data as synchronization. The model building comprises: separating effects of heart and respiratory motion; assessing beat-to-beat variation in coronary motion; and, eliminating outliers. The method then uses the model to predict remaining motion of the coronary for subsequent high-resolution data acquisition mode. Imaging of the artery is obtained from the acquired high-resolution data.

In accordance with one feature of the invention, a method is provided for imaging, comprising: predicting from multiple real time imaging data, motion of an object; and obtaining high-resolution imaging data of the object using the predicted motion.

In accordance with the invention a method is provided for imaging, comprising: measuring motion of an object using the real time imaging data in specific spatial orientations during a real-time data acquisition mode; and using the measured motion to predict the location of the object at a later time in during a subsequent high-resolution image acquisition mode.

In one embodiment, motion of each of a plurality of coronary arteries is measured directly (i.e., using the real time images that contain the coronary artery). The process then derives the motion of the coronary from such directly measured images. Prior art did indirect estimates of coronary motion—for example by assuming coronary motion proportional to heart wall motion or proportional to diaphragm motion and assumed that the motion was reproducible from beat to beat using real time imaging in specific spatial orientations. The measured motion is used to predict the location of each of the arteries at a later point in the cardiac cycle along with the time of acquisition. The measured motion is also used to predict the optimal timepoint in each heart cycle, and the location and timepoint are then used for high resolution imaging.

With such method, there are no assumptions about the motion of the coronary artery because it is measured directly. Also, there is no assumption that motion between time of detection and time of high-resolution acquisition remains constant, so rapid or irregular motion patterns do not affect the imaging.

In one embodiment, a method for imaging includes: operating in a real-time imaging data acquisition mode to obtain real time imaging data; determining motion of a coronary artery using the obtained real time imaging data; predicting, from the determined motion, the location of the artery at later points in a cardiac cycle; and, operating in a high-resolution data acquisition mode to obtain high-resolution imaging data of the artery using the predicted location of the artery.

In one embodiment, the method includes extracting coronary position from images acquired using real time data. Using such real time data acquired images and electrocardiogram (ECG) data, the method builds a model (in the detailed description we do not describe this model building directly coronary motion using the real time image data based on the current and past heartbeats obtained from the ECG data. The model building comprises: separating effects of heart and respiratory motion; assessing beat-to-beat variation in coronary motion; and, eliminating outliers. The method then uses the model to predict remaining motion of the coronary for subsequent a high-resolution data acquisition mode. Imaging of the artery is obtained from the acquired high-resolution data.

In one embodiment, the method uses a priori knowledge of the primary direction of motion of each of the three major arteries with respect to a heart orientation. The LAD coronary artery primarily moves in the z direction, while LCX and RCA coronaries move primarily in the x-y plane. The z motion of the LAD can also be used to correct for bulk motion in that direction also affecting the LCX and RCA coronary arteries. The z motion of the LAD can also be used to correct bulk motion in that direction. The method measures the motion of each of these coronary arteries directly, using the real time imaging data in specific orientations, and then uses the measured motion to predict the location of each artery at a later point in time in the cardiac cycle, used for the high-resolution image acquisition.

In one embodiment, a method for imaging an anatomical organ includes: using real time data of specific planes of the anatomical organ to build a model of the organ; using the model to predict motion of the organ; wherein the model predication comprises: separating effects of the organ motion from other sources of motion; and assessing cycle to cycle variation in the organ motion.

In one embodiment, the model predication includes eliminating outliers.

The details of one or more embodiments of the invention are set forth in the accompanying drawings and the description below. Other features, objects, and advantages of the invention will be apparent from the description and drawings, and from the claims.

DESCRIPTION OF DRAWINGS

Like reference symbols in the various drawings indicate like elements.

DETAILED DESCRIPTION

Figure 1:
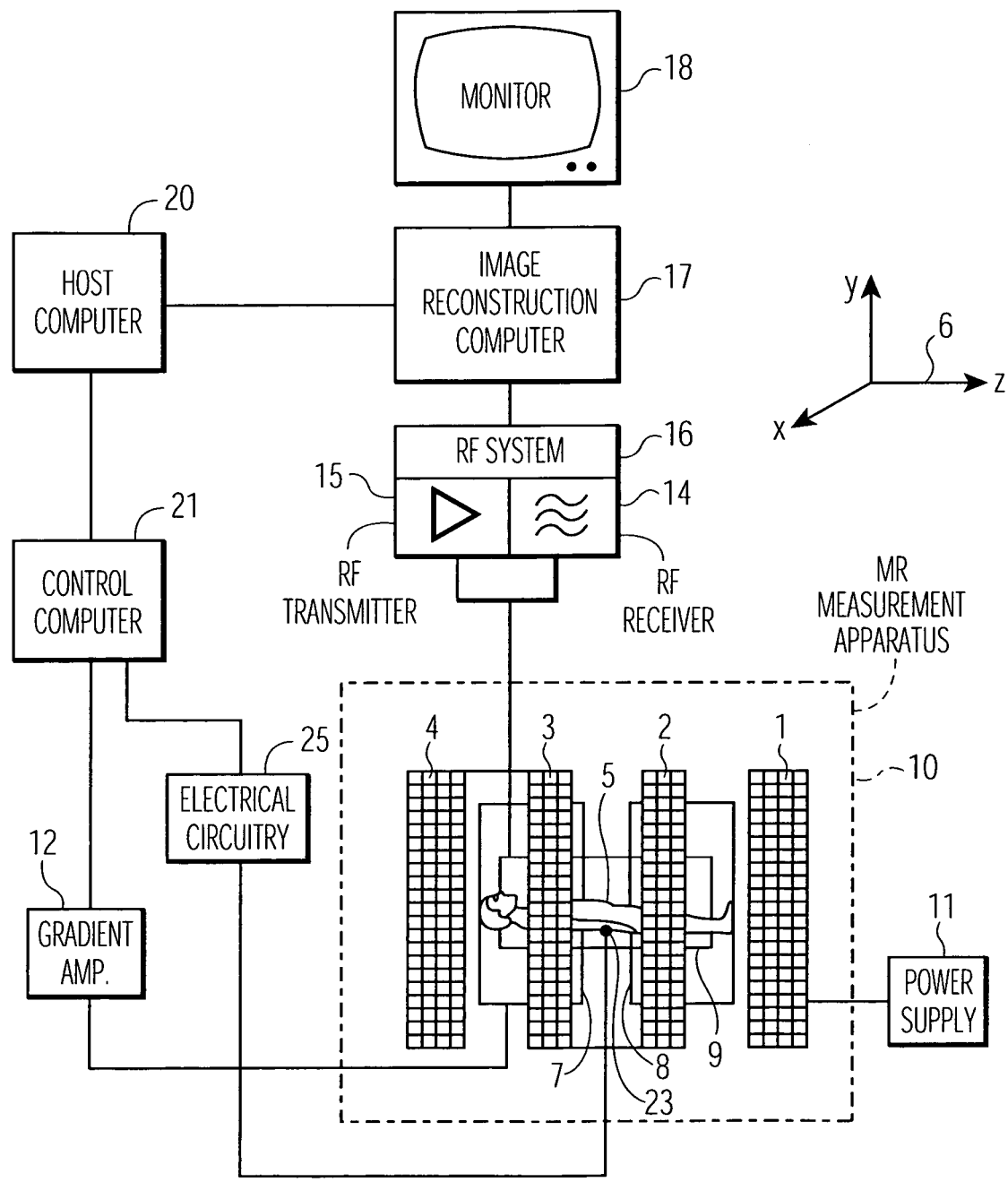
FIG. 1 is a schematic of nuclear magnetic resonance (MR) tomographic imaging apparatus in which the inventive method and apparatus can be employed.

Referring now to FIG. 1, nuclear magnetic resonance (MR) tomographic imaging apparatus is shown. It is noted that the MR apparatus is adapted to operate selectively in either a real time MR imaging data acquisition mode or a high-resolution MR imaging data acquisition mode.

Figure 2:
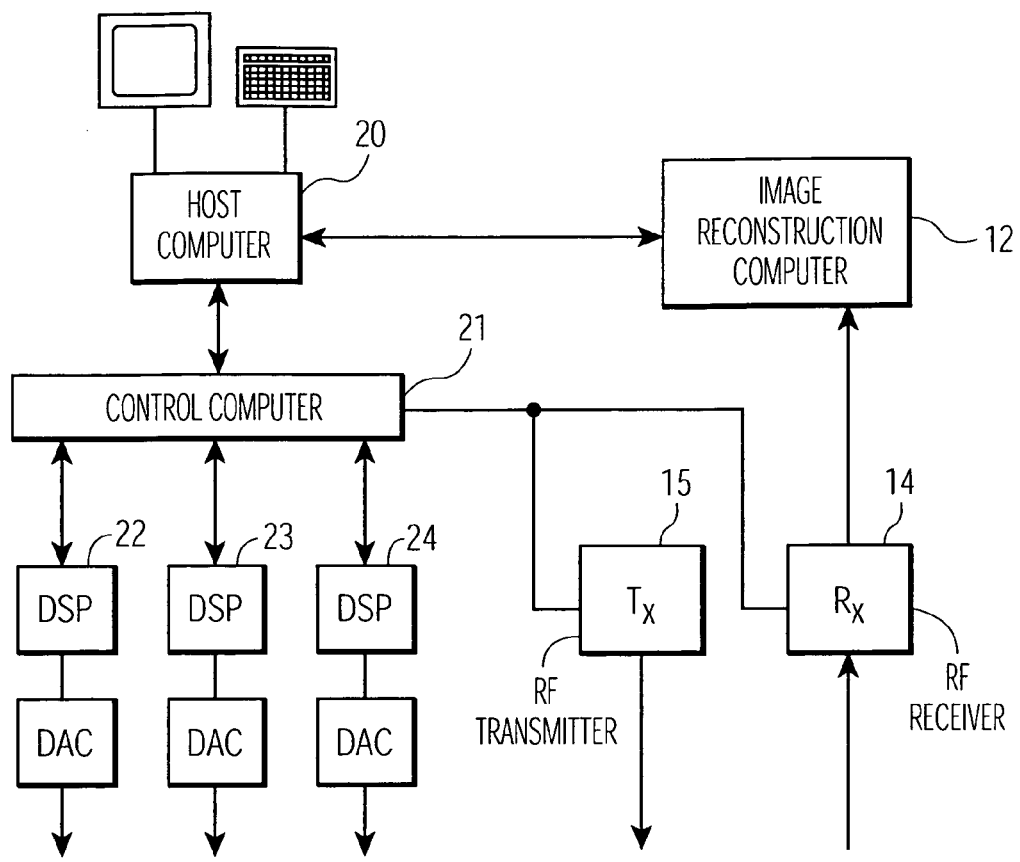
FIG. 2 is a block diagram of the structure of the system controller of the apparatus of FIG. 1 in greater detail.

The apparatus includes a magnet system including coils 1 through 4 which generate a uniform basic field, fed by a power supply 11. Gradient coil systems 7, 8 that are driven by a gadient amplifier 12 are provided in the magnet system. The gradient coil systems 7, 8 are implemented for generating magnetic field gradients in three spatial directions x, y, z of a coordinate system 6. The examination subject 5 is surrounded by a radio-frequency antenna 9 that is connected to a radio-frequency transmission unit 15 as well as to a radio-frequency reception unit 14 disposed outside of the measurement apparatus 10. The radio-frequency transmission unit 15 and the radio-frequency reception unit 14 are components of a radio-frequency system 16 in which, among other things, the received signals are sampled and demodulated in a phase-sensitive manner. An image is produced from the demodulated signals with an image reconstruction computer 17, forwarded to a host computer 20 having a memory for storing, inter alia, acquired MR imaging data and a program for operating the MR apparatus including a program to be described in connection with FIG. 3, and displayed on a monitor 18. The entire unit is driven by a control computer 20. The hardware control is assumed by a control computer 21 that is connected to the host computer 20. Cardiac electrodes 23 are connected to the patient. Electrical circuitry 25 is be used to analyze the patient's cardiac cycle and to output trigger signals to the computer 20 via computer control 21 at appropriate times during the cardiac cycle. The entire system control is shown in somewhat greater detail in FIG. 2.

The control computer 21 contains a standard CPU on which the actual measuring sequence is executed. At least one radio-frequency transmission unit 15, at least one radio-frequency reception unit 14 and three digital signal processors (DSP) 22, 23 and 24 are coupled to this CPU. Via interrupts, the gradient DSPs 22, 23 and 24 can request data from the controller CPU as soon as their local buffers have been emptied. There is also a digital connection to the image reconstruction computer 17 in order to synchronize the data acquisition with the image reconstruction. A bus to the host computer 20 maintains a real-time connection between the host and the controller CPU in order to provide the user with the possibility of also influencing the measuring execution during the measurement.

Figure 3:
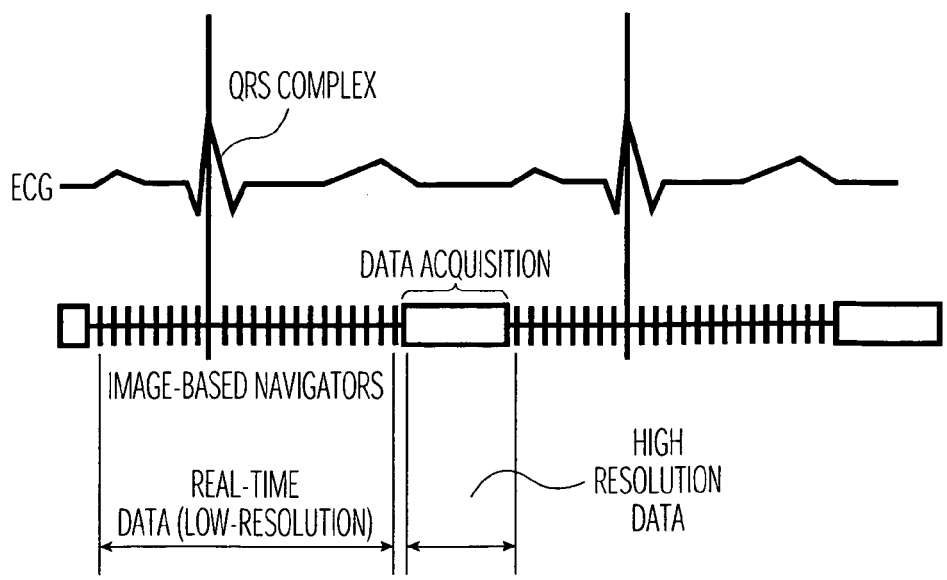
FIG. 3 is timing diagram showing the relationship between a QRS complex in a cardiac heart cycle and a real time, low-resolution data acquisition mode and a subsequent high-resolution data acquisition mode.
Figure 4:
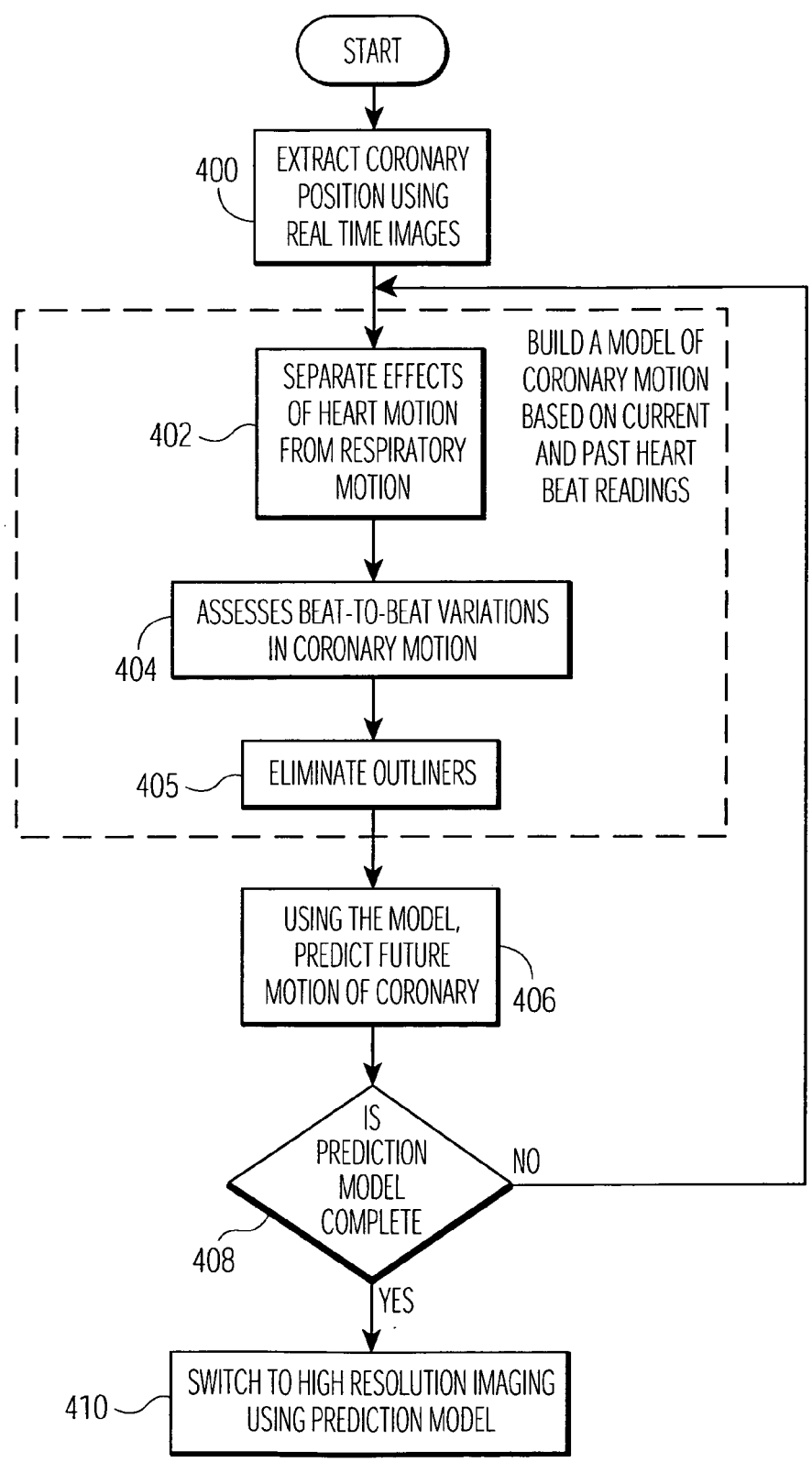
FIG. 4 is a general flow diagram of a method for obtaining MR imaging data according to the invention.

Referring now to FIG. 4, a flow diagram is shown of the basic steps of the process for obtaining MR imaging data according to the invention. In general, motion of each of a plurality of coronary arteries is measured directly using real time, low resolution imaging data in specific spatial orientations. Here, real time images are images low spatial resolution, moderate temporal resolution images, each acquired in a single short period of 30-50 ms taken along the point of heart compression shown for the QRS complex in FIG. 3.

The measured motion is used to predict the location of each of the arteries at a later point in the cardiac cycle. The predicted motion is then used for high-resolution image acquisition mode, shown in FIG. 3. Here, high-resolution images are high spatial resolution, high temporal resolution images, each acquired over 8-10 heartbeats. During the high-resolution imaging mode, real time motion correction, i.e., "on the fly" adjustment of the imaging plane is made to move the plane to where the object of interest is located at the current point in time as predicted by the data obtained by the low resolution imaging mode. More particularly, imaging is performed in real time from the beginning of the heart cycle (R-wave) to a specific point in the cardiac cycle, as shown in FIG. 3. The motion of the coronaries is extracted also in real-time from these images. The motion of the coronaries in the next 100-200 ms is then predicted, based on the current detected motion and the prior recent history of motion. Image acquisition then proceeds with new slice position coordinates based on the extracted motion.

More particularly, and referring to FIG. 4, the system is activated to extract coronary position using real time images, Step 400.

The real time images are used to build a model of coronary motion based on current and past heart beat reading. More particularly, in Step 402, the real data are processed using any convention technique such as Fourier analysis to separate the effect of coronary motion from respiratory motion. Next, the process assesses variations in coronary motion from heartbeat to heartbeat, Step 404. By determining representative motion patterns averaged over some number of prior heartbeats, the process can eliminate heartbeats with motion that is determined to be too different from the mean motion pattern (i.e., outliers, a deviation substantially greater from the mean data points), Step 405. Having built a model of coronary motion based on current and past heart beat reading, the process uses the model to predication future coronary motion (i.e., the process generates a predicated trajectory of the coronary), Step 406.

The model is built until it is complete, Step 408.

When the model is complete, the system operates in a high-resolution data acquisition mode taking MR imaging data at predicted times and position estimates provided by the predicated trajectory of the coronary, Step 410.

Figure 5:
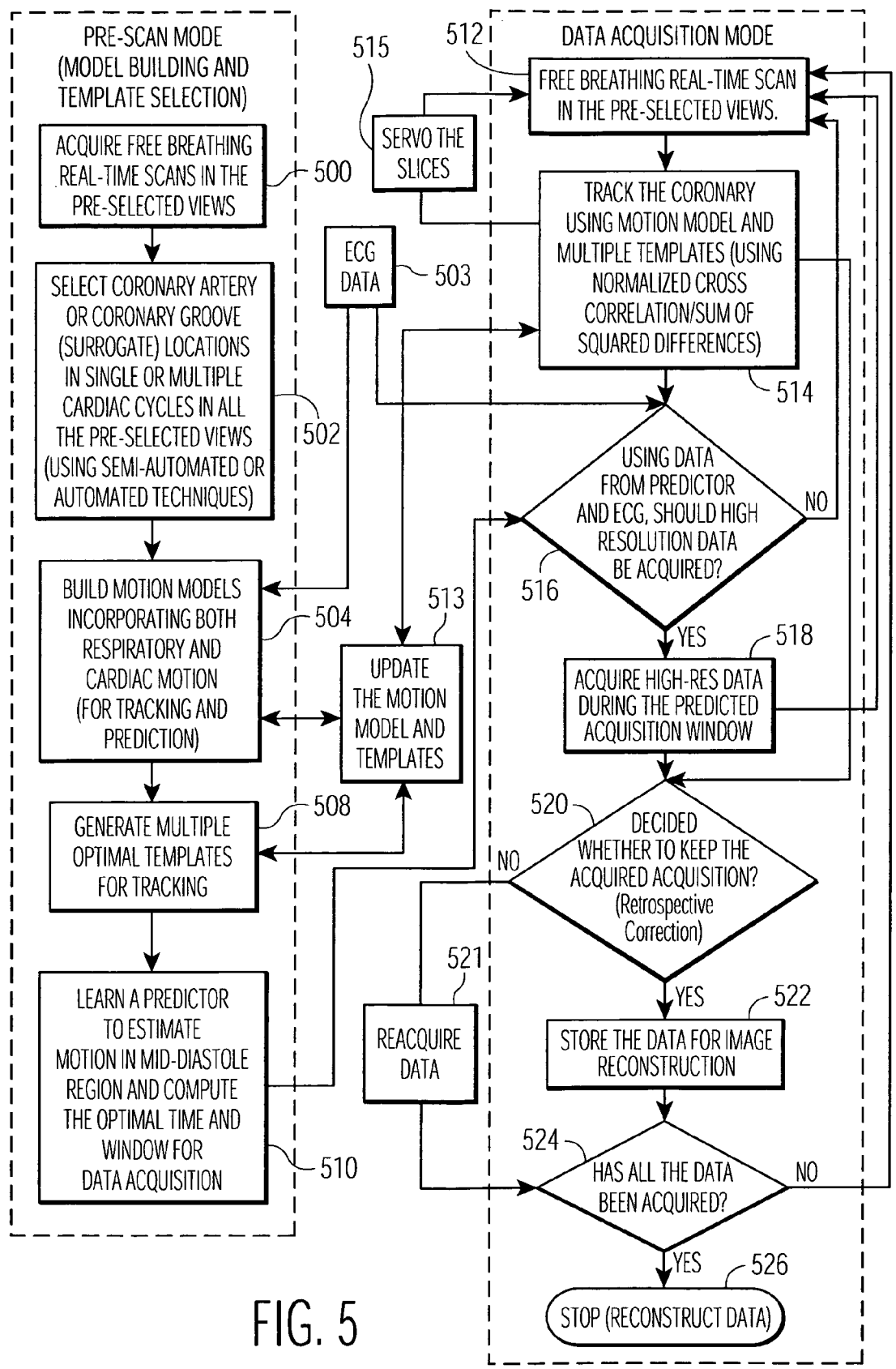
FIG. 5 is a more detailed flow diagram of the method for obtaining MR imaging data according to the invention.

Referring now to FIG. 5, a pre-scan mode is used to build the coronary trajectory described above in FIG. 4. Thus, in Step 500 the process acquires free breathing real time scans in preselected views of the coronary arteries. In order to track the coronary motion, one would ideally want to track the complete 3D motion of the coronaries. Due to the complex motion of the coronaries and the tradeoff between spatial and temporal resolution of the data acquired, the process restricts the imaging to two views; namely, the short axis and four-chamber view. In both these views, the left and right coronary arteries have quite large extent of motion representative of the coronary arteries is general. More particularly, the method uses a priori knowledge of the primary direction of motion of each of the three major arteries with respect to a heart orientation. The LAD coronary artery primarily moves in the z direction, while LCX and RCA coronaries move primarily in the x-y plane. The z motion of the LAD can also be used to correct for bulk motion in that direction also affecting the LCX and RCA coronary arteries. The z motion of the LAD can also be used to correct bulk motion in that direction.

In this example, the method includes extracting coronary position from images acquired using real time data. Using such real time data acquired images and electrocardiogram (ECG) data, the method builds a model of coronary motion using the real time image data based on the current and past heartbeats obtained using the ECG data as synchronization. The model building comprises: separating effects of heart and respiratory motion; assessing beat-to-beat variation in coronary motion; and, eliminating outliers. The method then uses the model to predict remaining motion of the coronary for subsequent high-resolution data acquisition mode. Imaging of the artery is obtained from the acquired high-resolution data.

Next, in Step 502, the process selects the coronary artery or surrogate locations (for example coronary groove which is almost always visible in the preselected views) within the coronary area in single or multiple cardiac cycles in all the preselected views using either any conventional semi-automatic or automated technique.

Next, the process builds models incorporating both respiratory and cardiac motion for using in trajectory predication and tracking, Step 504. It is noted that the motion building is synchronized with ECG data, Step 503. It is also noted that the data used to build the model is used for future updates and template generation, Step 513. Thus, the most recent trajectory model and templates are stored in the processor, Step 513 for use in the current motion model and for use during a subsequent high-resolution data acquisition mode.

The tracking algorithm used in this example, is a variation of normalized cross correlation with weighted template updating or multiple templates. The search for the maximum is localized to a small window around the center of the normalized cross-correlation matrix. An alternative is to track a weighted sum of the template image and the edge response. One can modify the tracking method by any of the following approaches:

Use of iterative techniques to improve and obtain sub-pixel accuracy.

Use of position and velocity also as feature values (normalized) to remove jitter. Also incorporation of some estimation filter like Kalman filter.

Use of robust statistics to remove outliers.

Use of rigid or affine registration for further refinement.

Local feature (corner, curvature, etc,) for refinement (i.e., better accuracy).

After tracking the motion of the grooves the variability between cardiac cycles is estimated. The tracked data are first filtered (using both Savitzky-Golay filtering and Gaussian filters or any suitable technique) and then segmented using simple heuristics (using 2nd order derivatives to estimate troughs and crests corresponding to end diastoles and systoles). The variability in the motion of the bottom groove in the short axis view and the left groove is in the four chamber view is attributed to the fact that the respiratory motion affects both the x and y directions in as short axis view unlike the four-chamber view where it only affects the y-direction. Respiratory motion is estimated by tracking the motion of few regions around the heart in the same image sequences. The regions tracked are, in this example, the liver-lung interface (1), the liver-heart interface including the vessel (2), and the center of mass of the left ventricle (3). The jitter in the respiratory motion is removed by simple heuristics and the data are filtered with both the Savitzky-Golay and Gaussian filters.

In any event, multiple optimal templates are generated for tracking the position of the coronary, Step 508.

Next, the processor learns a predictor to estimate, here in the mid-diastole region, and computes the optimal time and position window for the coronary for use during the subsequent real-time data acquisition mode, Step 518, to be described. In Step 512, real time images are acquired in the pre-selected views. It is noted that Steps 500-510 are a one-time pre-scan mode performed to establish the motion model. In the data acquisition mode, the model derived in the prescan mode is used on a heartbeat by heartbeat basis to first acquire some real time data for that heartbeat, apply the decision making process to determine if that heartbeat should be used to acquire some of the high resolution data, and then carry on with Steps 518-526. Both modes are required since the prescan mode is used to optimize templates for the tracking, etc.

Next, in Step 514, the scans obtained in Step 512 are used to track the coronary using the updated motion model, Step 513, and multiple templates using, for example, conventional normalized cross correlation/sum of square differences, processing and conventional slice servoing techniques, Step 515.

Next, in Step 516, the process determines, from the predictor, Step 510, the result of the tracking in Step 514, and the time since the R-wave of the ECG (Step 503), whether high resolution data, of the coronary should be acquired, based on the degree of deviation of the current motion data from the range of motions predictable as determined in Step 510. If not, the process returns to Step 512. If the high-resolution data acquisition mode should be initiated, high-resolution data are acquired at the predicted slice position in the projected window, Step 518. It should be noted that once data are acquired in a particular cardiac cycle, the process moves back to the real-time scanning and tracking mode, Step 512, and the process repeats.

Next, the process determines whether to keep or discard the high-resolution data acquired in Step 518, by comparing the motion during that heartbeat to the predictable range of motions as determined in Step 510, including consideration of the time in the heart cycle as well as the absolute motion.

If not, the process reacquires data in the next heartbeat, Step 512; on the other hand, if the high resolution data is to be kept, it is stored for image reconstruction, Step 522.

Next, the process determines whether sufficient high-resolution data has been acquired according to the spatial resolution requirements of the prescribed scan, Step 524. If not, the process returns to Step 512; on the other hand, if sufficient data has been acquired, the data acquisition mode ends, and the high resolution data are transferred using any conventional process to reconstruct the coronary artery images.

Thus, the method uses implementation of a pulse sequence that can switch between real time imaging, and high-resolution imaging. More particularly, the process includes: extracting coronary position in real time images; and building a model of coronary motion based on the current and past heartbeats. The model building includes: separating effects of heart and respiratory motion; assessing beat-to-beat variation in coronary motion; and eliminating outliers. Next, using the model, the method predicts the remaining motion of the coronary until the time of high-resolution acquisition.

Thus, from the discussion above, the process compensates for motion of the heart and arteries because of the effect of respiratory motion on the position of the heart/arteries and also compensates for the effect of contraction/expansion of the heart itself during a cardiac cycle. Data are taken through the contraction phase and into the beginning of the relaxation phase then used to take other data later in the relaxation phase. The process modifies the slice excitation (slice selection) and time of data acquisition based on where the predicted motion indicates the artery has moved. The process uses derived motion to build up a trajectory of motion of a specific object in the image, rather than to simply determine whether a particular frame is acceptable for use in building an image. The process starts with some a priori information about trajectory of periodic motion of an object and use this as input to the described method to constrain the parameter space. It is this derived trajectory, not motion in a particular frame that allows determination of where to image in the cardiac cycle in addition to determination of any slice shifting that must be done as compensation. The process uses the motion data to trigger a separate data acquisition phase.

A number of embodiments of the invention have been described. Nevertheless, it will be understood that various modifications may be made without departing from the spirit and scope of the invention. For example, the method could be used to track the bulk motion of the heart to acquire other types of cardiovascular MR data such as for perfusion imaging, infarct imaging, functional imaging in order to obtain spatially and temporally registered images. Another example would be to use the method for compensation for respiratory motion in the thorax or abdomen by applying the model derivation and tracking to appropriate regions. Further the method may be applied to other imaging processes such as ultrasound imaging. Accordingly, other embodiments are within the scope of the following claims.

What is claimed is:

1. A method for MR imaging, comprising:
    acquiring first low-resolution MR image data using an MR scanner during a first heart beat cycle in a pre-scan mode;
    measuring real-time motion of a coronary artery based on the acquired first low-resolution MR image data using an image processing device;
    building a model of coronary artery motion based on the measured real-time motion of the coronary artery from the acquired first low-resolution MR image data;
    tracking a position and predicting a trajectory of the coronary artery within the first particular heart beat cycle that the first low-resolution MR image data was acquired within based on the model of coronary artery motion using a computer system;
    predicting a first acquisition window based on the tracked position and predicted trajectory of the coronary artery;
    obtaining first high-resolution MR image data of the coronary artery at the predicted first acquisition window within the first particular heart beat cycle;
    acquiring second low-resolution MR image data using the MR scanner during a second heart beat cycle;
    measuring real-time motion of the coronary artery based on the acquired second low-resolution MR image data using the image processing device;
    updating the model of coronary artery motion based on the measured real-time motion of the coronary artery from the acquired second low-resolution MR image data;
    tracking a position and predicting a trajectory of the coronary artery within the second particular heart beat cycle based on the updated model of coronary artery motion using a computer system;
    predicting a second acquisition window based on the tracked position and predicted trajectory of the coronary artery; and
    obtaining second high-resolution MR image data of the coronary artery at the predicted second acquisition window within the second particular heart beat cycle.

2. The method of claim 1, wherein building the model of coronary artery motion comprises:
    separating effects of heart motion from respiratory motion;
    assessing beat-to-beat variations in coronary artery motion; and
    eliminating outliers.

3. The method of claim 1, wherein the low-resolution MR image data comprises images of low spatial resolution and moderate temporal resolution, each image acquired in a single short period of between 30 to 50 ms.

4. The method of claim 1, wherein the method is repeated for a sequence of 8 to 10 heartbeats.

5. The method of claim 1, wherein the predicted motion of the coronary artery covers a next 100-200 ms from currently detected motion.

6. The method of claim 1, wherein the coronary artery comprises one of the left anterior descending (LAD), the left circumflex artery (LCX), and the right coronary artery (RCA).

7. The method of claim 1, wherein real-time motion correction is performed using a tracking algorithm.

8. The method of claim 1, wherein prior to acquiring the first and second high-resolution MR image data, a determination is made that high resolution data should be acquired based on the predicting a trajectory of the coronary artery and ECG.

9. The method of claim 1, wherein after acquiring the first and second high-resolution MR image data, a determination is made as to whether to keep the acquired high-resolution MR image data or to reacquire the high-resolution MR image data.

* * * * *